United States Patent
Braun et al.

(10) Patent No.: US 6,821,948 B1
(45) Date of Patent: Nov. 23, 2004

(54) CONJUGATE FOR MEDIATING CELL, COMPARTMENT OR MEMBRANE-SPECIFIC TRANSPORT OF ACTIVE SUBSTANCES

(75) Inventors: Klaus Braun, Sandhausen (DE); Peter Peschke, Böhl-Iggelhelm (DE); Eckart Friedrich, Landau-Ilbesheim (DE); Rüdiger Pipkorn, Heidelberg (DE); Waldemar Waldeck, Laudenbach (DE); Jürgen Debus, Stettfeld (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 10/031,505
(22) PCT Filed: Jul. 14, 2000
(86) PCT No.: PCT/DE00/02346
§ 371 (c)(1), (2), (4) Date: Jul. 2, 2002
(87) PCT Pub. No.: WO01/05432
PCT Pub. Date: Jan. 25, 2001

(30) Foreign Application Priority Data

Jul. 16, 1999 (DE) .......................... 199 33 492

(51) Int. Cl.[7] .............................................. A61K 47/48
(52) U.S. Cl. ............................. 514/2; 514/13; 514/16; 514/44; 530/300; 530/326; 530/329; 530/345; 530/408; 530/409; 530/410; 536/23.1
(58) Field of Search .................... 514/2, 8, 12, 21, 514/13, 16, 44; 530/300, 324, 326, 329, 345, 350, 402, 408, 409, 410; 536/23.1

(56) References Cited

U.S. PATENT DOCUMENTS

| | | | |
|---|---|---|---|
| 5,661,025 A | * | 8/1997 | Szoka et al. ................. 435/458 |
| 5,670,347 A | * | 9/1997 | Gopal .......................... 435/467 |
| 5,674,977 A | * | 10/1997 | Gariepy ....................... 530/324 |
| 5,877,282 A | * | 3/1999 | Nadler et al. ................ 530/350 |
| 6,303,576 B1 | * | 10/2001 | Blaschuk et al. ............. 514/14 |

FOREIGN PATENT DOCUMENTS

| | | | | |
|---|---|---|---|---|
| FR | 2 786 397 | | 6/2000 | ...................... 38/16 |
| FR | 2 787 793 | | 6/2000 | ....................... 5/87 |
| WO | WO 97/12912 | | 4/1997 | ...................... 14/47 |
| WO | WO-97/28822 | A1 * | 8/1997 | |
| WO | WO 00/01417 | | 1/2000 | ...................... 47/48 |
| WO | WO 00/58488 | | 10/2000 | ...................... 15/87 |

OTHER PUBLICATIONS

Pietersz, Geoffrey A., Li, Wenjun, Apostolopoulos, Vasso 2001. A 16-mer peptide (RQIKIWFQNRRMKWKK) from antennapedia preferentially targets the Class 1 pathway. Vaccine 19:1397–1405.

Mi, Zhibao, Mai, Jeffrey, Lu, Xiaoli, & Robbins, Paul D. 2000. Characterization of a Class of Cationic Peptides Able to Facilitate Efficient Protein Transduction *in Vitro* and *in Vivo*. Molecular Therapy, vol. 2, No. 4: 339–347.

(List continued on next page.)

Primary Examiner—Jeffrey Edwin Russel
(74) Attorney, Agent, or Firm—Marianne Fuierer; Steven J. Hultquist; Yongshi Yang

(57) ABSTRACT

The present invention relates to conjugates for mediating a cell-specific, compartment-specific or membrane-specific to methods of active substances. The invention also relates to methods of preparing these conjugates as well as their use. The conjugates comprise:
  a transport mediator for the cell membrane,
  a cell-specific, compartment-specific or membrane-specific address protein or peptide, and
  an active substance to be transported.

20 Claims, 8 Drawing Sheets

OTHER PUBLICATIONS

Derossi, Daniele, Chassaing, Gerard & Prochiantz, Alain 1998. Trojan peptides: the penetratin system for intracellular delivery. Trends in Cell Biology vol. 8: 84–86.

Rouselle, Christophe, Clair, Philippe, Lefauconnier, Jeanne–Marie, Kaczorek, Michel, Scherrmann, Jean–Michel & Temsamani, Jamal 2000. New Advances in the Transport of Doxorubicin through the Blood–Brain Barrier by a Peptide Vector–Mediated Strategy. Molecular Pharmacology, 57:679–686.

Pooga, Margus, Soomets, Ursel, Hällbrink, Mattias, Valkna, Andres, Saar, Külliki, Rezaei, Khadijeh, Kahl, Ulrika, Hao, Jing–Xia, Xu, Xiao–Jun, Wiensenfeld–Hallin, Zsuzsanna, Hökfelt, Tomas, Bartfai, Tamas, Langel, Ülo 1998. Cell penetrating PNA constructs regulate galanin receptor levels and modify pain transmission in vivo. Nature Biotechnology vol. 16: 857–861.

Akhtar, Saghir, Basu, Soumitra, Wickstrom, Eric & Juliano, R.L. 1991. Interactions of antisense DNA oligonucleotide analogs with phospholipid membranes (liposomes). Necleic Acids Research, vol. 19, No. 20: 5551–5559.

Bennett, C.F., Mirejovsky, D., Crooke, R.M., Tsai, Y.J., Felgner, J., Sridhar, C.N., Wheeler, C.J. & Felgner, P.L. 1997. Structural Requirements for Cationic Lipid Mediated Phosphorthioate Oligonucleotides Delivery to Cells in Culture, Journal of Drug Targeting, vol. 5, No. 3: 149–162.

Cosset, F–L, Russell, Sj 1996. Targeting retrovirus entry. Gene Therapy 3:946–956.

Bilbao, Guadalupe, Feng, Meizhen, Rancourt, Claudine, Jackson, Jr., William H., Curiel, David T. 1997. The FASEB Journal vol. 11: 624–634.

Gao, X & Huang, L. 1995. Gene Therapy 2:710–722.

* cited by examiner general diagram for Fmoc synthesis

Cellular take-up of the conjugate according to the invention

Time-dependent intracellular transport of the modules. (Z): cytoplasm; (N): nucleus; (+): positive signal; (−): no signal. Final conjugate concentration: 100 pM

| Transporter | incubation period [h] | Z | N | method |
|---|---|---|---|---|
| Alexa™(L)-Penet-S-S-(L)-NLS-KK^(Rhod110)-PNA | 1 | + | + | CLSM |
| | 3 | + | + | |
| | 6 | + | + | |
| | 10 | membrane spots | + | |
| | 24 | membrane spots | + | |
| Alexa™(L)-PTD(TATHIV-1)-S-S-(L)-KK^(Rhod110)-PNA | 1 | + | − | CLSM |
| | 3 | + | − | |
| | 6 | + | − | |
| | 10 | − | − | |
| | 24 | − | − | |
| Alexa™(L)-TP(IAOP/EGn)-S-S-(L)-NLS-KK^(Rhod110)-PNA | 1 | + | + | CLSM |
| | 3 | + | + | |
| | 6 | + | + | |
| | 10 | − | + | |
| | 24 | − | + | |
| Alexa™(L)-TP(IAOP/EGn)-S-S-(L)-KK^(Rhod110)-PNA | 1 | + | − | CLSM |
| | 3 | + | − | |
| | 6 | + | − | |
| | 10 | − | − | |
| | 24 | − | − | |

Fig. 8

CONJUGATE FOR MEDIATING CELL, COMPARTMENT OR MEMBRANE-SPECIFIC TRANSPORT OF ACTIVE SUBSTANCES

CROSS-REFERENCE TO RELATED APPLICATIONS

This application is filed under the provisions of 35 U. S. C. §371 and claims the priority of International Patent Application No. PCT/DE00/02346 filed Jul. 14, 2000, which in turn claims priority of German Patent Application No. 199 33 492.7 filed Jul. 16, 1999.

The present invention relates to conjugates for mediating cell-specific, compartment-specific or membrane-specific transport of active substances. The invention also relates to methods of producing said conjugates and their use.

As is known, cellular membrane systems are largely impermeable to many substances (e.g. nucleic acids, proteins, chemical substances) which shall be introduced into a cell from outside. For the introduction of nucleic acids it is possible to penetrate cell membranes by physical processes (transfection in the case of eukaryotes, transformation in the case of prokaryotes) and biological processes (infection). In the case of transformation, i.e. the direct take-up of the naked nucleic acid by the cell, the cells are treated beforehand. Various methods are available to produce these "competent cells". Most methods are based on the observations made by Mandel and Higa (J. Mol. Biol. 53, pages 159–163 (1970)) who were the first to show that it is possible to substantially increase the yields occurring when lambda-DNA is taken up by bacteria in the presence of calcium chloride. This method was used successfully for the first time by Cohen et al. (Proc. Natl. Acad. Sci. U.S.A. 69, pages 2210–2114 (1972)) for plasmid DNA and has been improved by many modifications. Another transformation method is based on the observation that high-frequency alternating-current fields can break up cell membranes (electroporation). This technique can be utilized to insert naked DNA not only in prokaryotic cells but also in eukaryotic cell systems (Weaver et al., J. Cell Biochem. 51, pages 426–435 (1993)). Two very mild methods of introducing DNA into eukaryotic cells were developed by Sikes et al. (Hum. Gen. Therap. 5, pages 837–840 (1994)) and Yang et al. (Proc. Natl. Acad. Sci U.S.A. 87, pages 9568–9572 (1990). They are based on the direct injection of the DNA into single cells (microinjection) and on the bombardment of a cell population using microprojectiles of tungsten on the surface of which the corresponding nucleic acid was bound (gene gun), respectively. In a progress parallel to the physical transformation of cells, biological infection methods have proved their efficiency. They comprise in particular the viral introduction of nucleic acids into cells (Chatterjee et al., Science 258, pages 1485–1486 (1992); Cossett and Rusell, Gene Therapy 3, pages 946–956 (1996); Bilbao et al., FASEB J. 11, pages 624–634 (1997)) and the liposome-mediated lipofection (Bennett et al., J. Drug Targeting 5, pages 149–162 (1997)). Reference is also made to standard methods of the liposomal transport (Gao and Huang, Gene Therapy 2, pages 710–722 (1995); Akhtar et al., Nucl. Acid. Res. 19, pages 5551–5559 (1991)) and poly-L-lysine formation (Leonetti et al., Bioconj. Chem. 1(2), page 149 (1990) of active substances to be able to transport them into cells.

Despite the above-listed plurality of methods of passing through the cellular membrane systems, there is no universal method serving for introducing different active substances into cells. All of the above-mentioned physical and biochemical methods are artificial and non-physiological unless they make use of cell-immanent mechanisms. It is presently not yet certain that viruses used as transport vehicles are free of toxicity. They are often not effective and, in addition, they are detected by the immune system.

It was therefore the object of the present invention to provide a possibility of permitting the site-directed and specific introduction of active substances into cells and compartments. The following demands must be complied with in this connection:

universal applicability cell-specific, compartment-specific and membrane-specific introduction behavior high degree of effectiveness low immunogenicity minimization of the infection risk sufficiently long residence time.

This object is achieved by the subject matters defined in the claims.

The inventors developed a conjugate comprising the following components:

a transport mediator for the cell membrane ("P"), a cell-specific, compartment-specific or membrane-specific address protein or peptide ("AP"), and an active substance to be transported ("W").

The conjugate according to the invention is preferably composed as follows:

P-AP-W

More preferably it comprises a spacer ("SP"):

P-AP-SP-W

The transport mediator for the cell membrane (abbreviated as "P" above) is a peptide or protein which can penetrate the plasma membrane. The length of this peptide or protein is not subject to limitation as long as it has the above property. Examples of "P" are derived preferably from the penetratin family (Derossi et al., 1998, *Trends Cell Biol.* 8, pages 84–87) or are transportan or parts thereof (Pooga et al., The Faseb Journal (1998), Vol. 12, page 68 et seq.), those of the penetratin family being preferred. An example of "P" is a penetratin having the following sequence:

$NH_2$-RQI KIWFQNRRMKWKK-(SEQ ID NO.: 1)

(NH2-Arg-Gln-Ile-Lys-Ile-Trp-Phe-Gln-Asn-Arg-Arg-Met-Lys Trp-Lys-Lys)

Further examples of the transport protein "P" are as follows:

Viral transport protein

PTD protein transduction domain (TAT/HIV-1)

1—letter code $H_2$N-YGRKKRRQRRR-COOH (SEQ ID NO: 12)

3-letter code $H_2$N-Tyr-Gly-Arg-Lys-Lys-Arg-Arg-Gln-Arg-Arg-Arg-

Bacterial transport molecule

TP protein transport domain TP(Eco)

1-letter code $H_2$N-MTRQTFWHRIKH-CQOH (SEQ ID NO: 13)

3-letter code H2N-Met-Thr-Arg-Gln-Thr-Phe-Trp-His-Arg-Ie-Lys-His

The select "P" sequence is produced biologically (purification of natural transport mediator proteins or cloning and expression of the sequence in a eukaryotic or prokaryotic expression system), preferably synthetically, e.g. according to the established Merrifield method (Merrifield, J. Am. Chem. Soc. 85: 2149, 1963).

The selection of the address protein or peptide (abbreviated as "AP" above) depends on the membrane or membrane system which has to be penetrated and the target compartment of the cell (cytoplasm, nucleus, mitochondria, chloroplast, endoplasmic reticulum) or the cell organelle which shall be reached. The length of this address peptide or protein is not subject to limitation as long as it comprises the property of ensuring a cell-specific, compartment-specific or membrane-specific transport. For the introduction of active substances, in particular nucleic acids, "APs" are generally used which contain a cell-specific, compartment-specific or membrane-specific recognition signal, directing the attached active substance to its site of action. There are the "APs" to chose from which can transport active substances in the presence or absence of a membrane potential. The pure address sequence is usually sufficient for a transport into the cell compartment. However, it is also possible to chose "APs" which have a cell-specific or compartment-specific peptidase cleavage site. In the most favorable case, this cleavage site lies within the signal sequence but it can also be attached thereto by additional amino acids to ensure the cleavage of the address sequence after the target compartment is reached. The select "AP" sequence is produced biologically (purification of natural transport mediator proteins or cloning and expression of the sequence in a eukaryotic or prokaryotic expression system), preferably synthetically, e.g. according to the established Merrifield method (Merrifield, J. Am. Chem. Soc. 85: 2149, 1963). Examples of address proteins or peptides are as follows:

Import into the ER $H_3N+$-Met-Met-Ser-Phe-Val-Ser-Leu-Leu-Leu-Val-Gly-Ile-Leu-Phe-Trp-Ala-Thr-Glu-Ala-Glu-Gln-Leu-Thr-Lys-Cys-Glu-Val-Phe-Gin-(SEQ ID NO: 2);

Reimport into the ER $H_2N$-Lys-Asp-Glu-Leu-$COO^-$ (SEQ ID NO: 3);

Import into the mitochondria $H_3N+$-Met-Leu-Ser-Leu-Arg-Gln-Ser-Ile-Arg-Phe-Phe-Lys-Pro-Ala-Thr-Arg-Thr-Leu-Cys-Ser-Ser-Arg-Tyr-Leu-Leu-(SEQ ID NO: 4);

Import into the nucleus—Pro-Pro-Lys-Lys-Lys-Arg-Lys-Val (SEQ ID NO: 5);

$H_3N+$-Pro-Lys-Lys-Lys-Arg-Lys-Val-(=nuclear localisation sequence from 5V40-T antigen) (SEQ ID NO: 6);

Import into peroxisomes $H_2N$-Ser-Lys-Leu-$COO^-$ (SEQ ID NO: 7); and

Binding to the cell membrane $H_3N+$-Gly-Ser-Ser-Lys-Ser-Lys-Pro-Lys (SEQ ID NO: 8)

Furthermore, the conjugate may optionally contain a spacer (abbreviated as "SP" above) which is preferably located between the address protein/peptide and the active substance to be transported. However, it may also be located additionally or alternatively between the transport mediator and the address protein. The spacer serves for eliminating or positively influencing optionally existing steric interactions between the components. For example, the spacer may be selected from: polylysine, polyethylene glycol (PEG), derivatives of poly-methacrylic acid or polyvinyl pyrrolidone (PVP).

A redox cleavage site, e.g. -cysteine-S-S-cysteine-O—N—H—, is preferably present between the transport mediator and the address protein/peptide. The binding forming between transport mediator and address protein is a redox coupling (mild cell-immanent bond by means of DMSO; Rietsch and Beckwith, 1998, Annu. Rev. Gent 32, pages 163–84):

Cysteine-SH SH-cysteine---->cystine-S-S-cystine

The active substance or active agent (abbreviated as "W" above) is not subject to limitations. It can be chosen freely, depending on the effect which shall be produced in a cell. The active substance may be a diagnostic agent and/or a therapeutic agent. The conjugate may also comprise more than one active substance. The active substance may optionally be labeled, e.g. radioactively, with a dye, with biotin/avidin, etc. The active substance may be a nucleic acid, a protein or peptide, a chemical substance, etc. The next ones are mentioned by way of example: cDNA, genomic DNA, complete genes, regulatory elements, transcription factors, molecular probes, oligonucleotides, mRNA, mTRNA, antisense RNA, antisense oligonucleotides, plasmids, viral DNA, synthetic nucleotides, PNA (peptide nucleic acids), single amino acids and their derivatives, peptides, proteins, monoclonal and/or polyclonal antibodies, pharmaceutical active substances, chemotherapeutic agents, dyes, sensitizers, particles.

The conjugate elements "P" and "AP" are preferably synthesized synthetically according to the Merrifield method (Merrifield, J. Am. Chem. Soc. 85: 2149, 1963). The coupling of the other constituents (e.g. spacer and/or active substance) thereto is made by covalent chemical binding. The redox cleavage site is inserted chemically between "P" and "AP" by the above-mentioned redox coupling. There is also a covalent bond, preferably an acid amide bond, between an optionally present spacer and the active substance or the address protein and the active substance. Possible alternatives are ether or ester bonds, depending on the functional group(s) present in the substance to be conjugated.

The conjugate is preferably synthesized in the following steps:

1) separate peptide snythesis of "P", "AP" and, if applicable, the spacer (e.g. according to the Merrifield method)

2) covalent bond between "AP" and active substance, if applicable, with a spacer in between, 3) redox coupling of the product from step 2) with "P" by means of redox coupling (e.g. in water/DMSO)

4) purification (e.g. by means of HPLC).

The conjugates according to the invention have the advantage that irrespective of the kind and size of an active substance they can introduce it into cells and transport it into the desired cell compartment. Thus, an improvement of diagnostics and therapy in human and veterinary medicines and an application in scientific research can be anticipated. In partiuclar, the gene therapy can expect a boom on account of the conjugates according to the invention since complete genes including their regulatory elements become transportable. However, all of the other active substances can also be transported more specifically to the site of action by means of the conjugates according to the invention, which reduces the occurrence of undesired side effects. It was found that conjugates up to 25 MDa can be introduced into the cell interior. Moreover, apoptosis is often triggered, which might be a desired effect. The conjugates according to the invention distinguish themselves by a universal usability on account of their cell-specific, compartment-specific and membrane-specific introduction behavior.

The invention is described in more detail by means of the attached figures.

| Transport module | S-S | Address Module | Spacer | Active Substance |
|---|---|---|---|---|
| Penetratin-1 SEQ ID NO: 1 | S-S | NLS SEQ ID NO: 6 | Lys/Glyc | PNA; DNA; S-ODN |
| PTD$^{TAT/HIV-1}$ SEQ ID NO: 12 | S-S | Endoplasm Retik SEQ ID NO: 2 | Lys/Glyc | ANTIBODY |
| TP1$^{AOPIEco}$ SEQ ID NO: 13 | S-S | Mitochon directed SEQ ID NO: 4 | Lys/Glyc | PRO-DRUGS |
| TPF$^{human}$ SEQ ID NO: 8 | S-S | Peroxis directed SEQ ID NO: 7 | Lys/Glyc | DRUGS |

Figure 6:
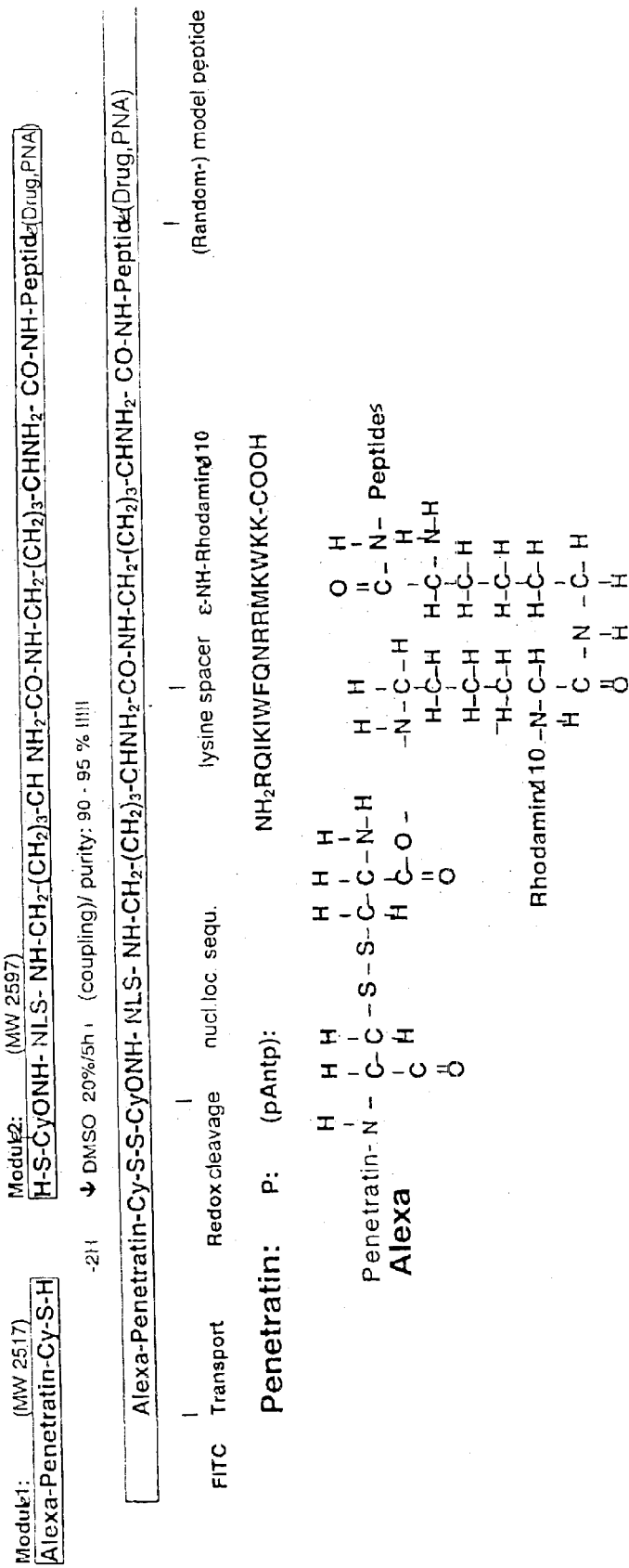

FIG. 6 shows the production of PNA constructs, wherein the constructs include transport protein RQIKIWFQNRRMKWKK-(SEQ ID NO: 1) and nuclear localization sequence PKKKRKV (SEQ ID NO 6) wherein the active substance was in one case a PNA having the sequence NH$_2$-TAC TGC GAC TCC GG-COOH (anti-sense with respect to rats P2 promoter c-myc=PNA$_{AS}$) (SEQ ID NO: 10) and then a non-sense (random) sequence having the sequence NH$_2$-TTA AGG AGG CTC-COOH (=PNA$_{NS}$) (SEQ ID NO: 11).

Figure 7:
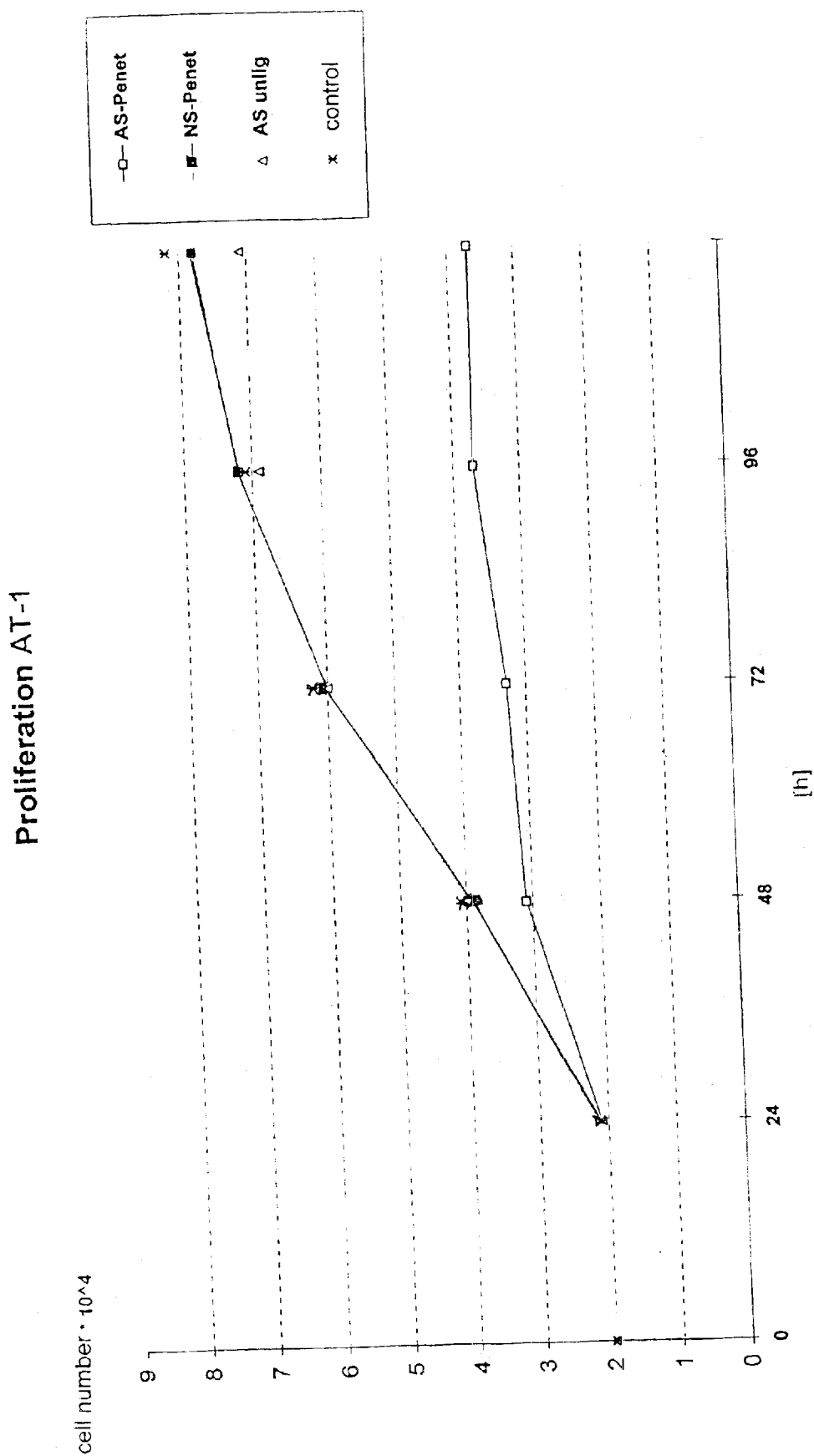

FIG. 7 shows the inhibition of the proliferation of AT-1 cells by introducing an anti-sense construct.

FIG. 8 shows the results of transport into the cytoplasm (Z) or the nucleus (N) for the conjugates produced in Example 1 for incubation periods of 1, 3, 6, 10 and 24 hours.

The invention is described in more detail by means of the following examples.

EXAMPLE 1

Figure 1:
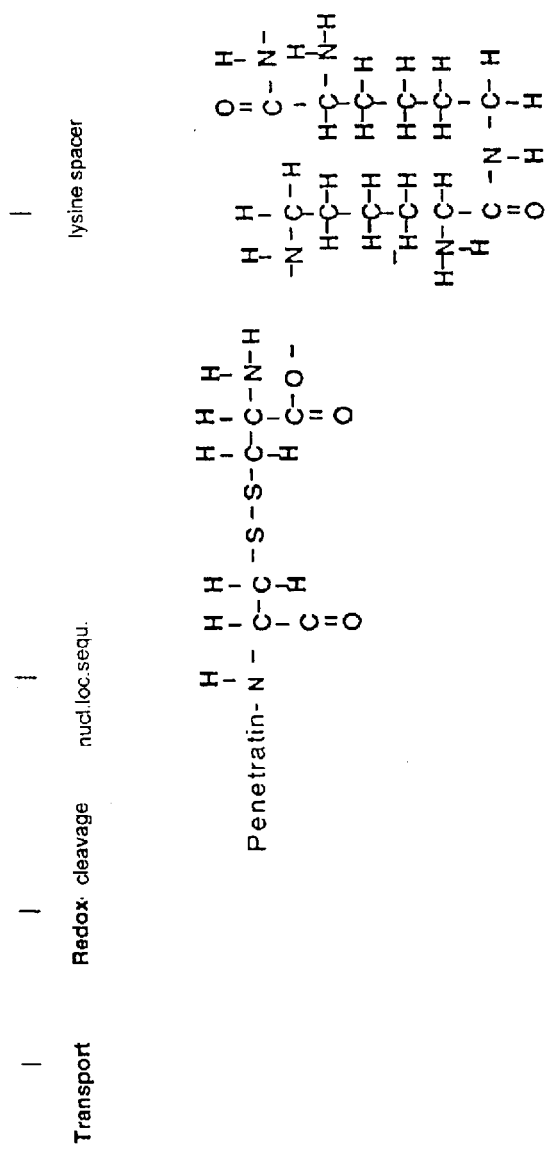
FIG. 1 shows a conjugate according to the invention and includes transport protein RQIKIWFONRRMKWKK-(SEQ ID NO: 1) and nuclear localization sequence PKKKRKV (SEQ ID NO 6)

Conjugate Comprising a Penetratin Constituent, an NLS, a Polylysine Spacer and Rhodamine Regarding the composition of the conjugate reference is made to FIG. 1.

Penetratin: NH$_2$-RQIKIWFQNRRMKWKK-

NLS (nuclear localisation sequence): NH$_2$-PKKKRKV

Figure 2:
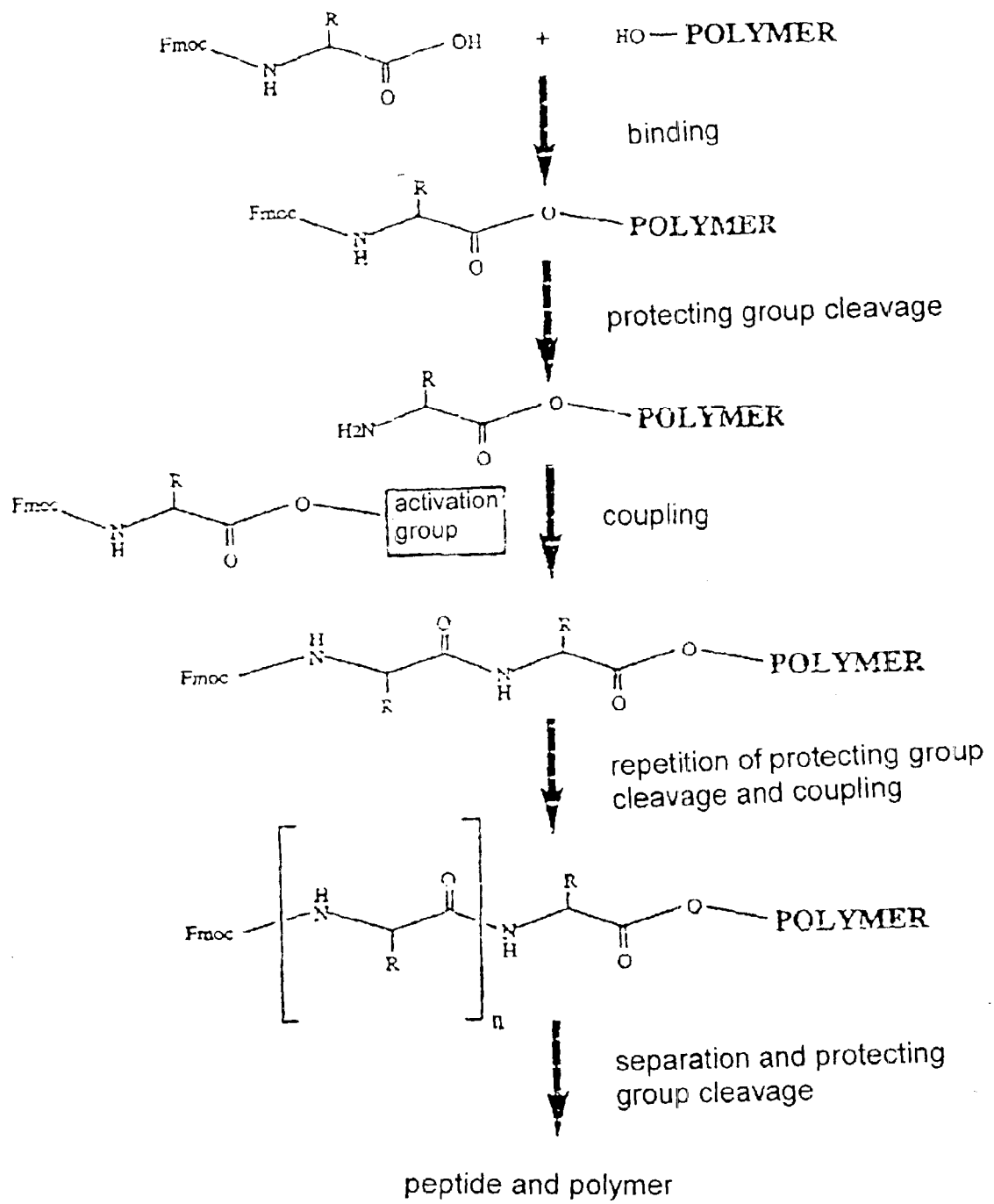
FIG. 2 shows a general diagram of the Fmoc synthesis.

Spacer (=(Lys) 2): NH—CH$_2$—(CH$_2$)$_3$—CHNH$_2$—CO—NH—CH$_2$—(CH$_2$)$_3$—CHNH$_2$—CO—NH Penetratin sequence, NLS and spacer were synthesized separately according to the standard Fmoc method ("peptides", H.-D. Jakubke, *Chemie and Biologie Spektrum*, Akad. Verl. 1996, ISBN 3-8274-0000-7). The general diagram of the Fmoc synthesis is shown in FIG. 2. For synthesizing the different component sequences, the first Fmoc amino acid (purchasable from Calbiochem GmbH, D-65796 Bad Soden, Germany) is initially attached to an insoluble polystyrene carrier resin via an acid-labile linker (=para-benzyl-oxybenzyl-alcohol-handle). Cleavage of the protecting group is achieved by treating the resin with 20% piperidine in dimethylformamide. The second Fmoc amino acid is linked using a preactivated species (e.g. succinimide, pentafluorophenylester or p-nitrophenylester groups present in the amino acid constituents) or using in situ activation, this was done in each case after the protecting group was removed from the preceding amino acid by basic treatment. Each further amino acid is coupled analogously. Having synthesized the desired peptide, it is removed from the carrier by treating it with 95% trifluoroacetic acid (TFA)+ 5% scavenger (e.g. triethylsilane), and the protecting groups are splitt off. The resulting crude peptides are purified by preparative HPLC on a YMC ODS-A 7A S-5 µm reversed-phase column (20×250 mm) using an elution agent containing 0.1% trifluoroacetic acid in water (A) or 60% aqueous actonitrile (B). The peptides were eluted with a successive linear gradient from 25% B to 60% B within 40 minutes at a flow rate of 10 ml/min. The fractions corresponding to the purified peptides were lyophilized.

The purified peptide components are treated together with 20% aqueous DMSO solution at room temperature for 5 hours, an oxidative coupling of the components resulting. For example, rhodamine 110 is coupled to the spacer as active substance to be transported. This is done by acid amide coupling at the free α-amino group of the lysine spacer. The complete conjugate is then purified by means of reversed-phase HPLC.

The further conjugates according to the invention were produced analogously:

$^{AlexaTM}$(L)-PTD$^{(TAT/HIV-1)}$-S-S-(L)-NLS-KK$^{(rhodamine110)}$-PNA $^{AlexaTM}$(L)-TP$^{(IAOP/ECO)}$-S-S-(L)-NLS-KK$^{(rhodamine110)}$-PNA PNA=NH$_2$-TTA AGG AGG CTC COOH (Example of active substance) (SEQ ID NO: 11)

Alexa 350=dye (Molecular Probes, U.S.)

EXAMPLE 2

Introduction of a Conjugate According to the Invention into Cells

AT-1 (rat prostate carcinoma) and DU-145 (human prostate carcinoma, ATCC HTB-81) cells were cultured in RPMI 1640, supplementd with 10% FCS, 2 mM glutamine, 100 U/min. penicillin, 100 µg/ml streptomycin.

For fluorescence correlation spectroscopy (FCS) AT-1 or DU-145 cells are grown on slides for 24 hours. Having changed the medium using dyestuff-free RPMI 1640 (without phenol red), the penetratin-containing conjugate of Exmaple 1 (100 nM) is placed onto the cells using RPMI and incubated at 37° C. and with 5% CO$_2$ for 5, 24 or 48 hours. Thereafter, the conjugate-containing medium is removed and washed twice with 200 µl of dyestuff-free RPMI and then measured by means of FCS. Laser excitation takes place at 488 nm and emission at 538 nm.

Figure 3:
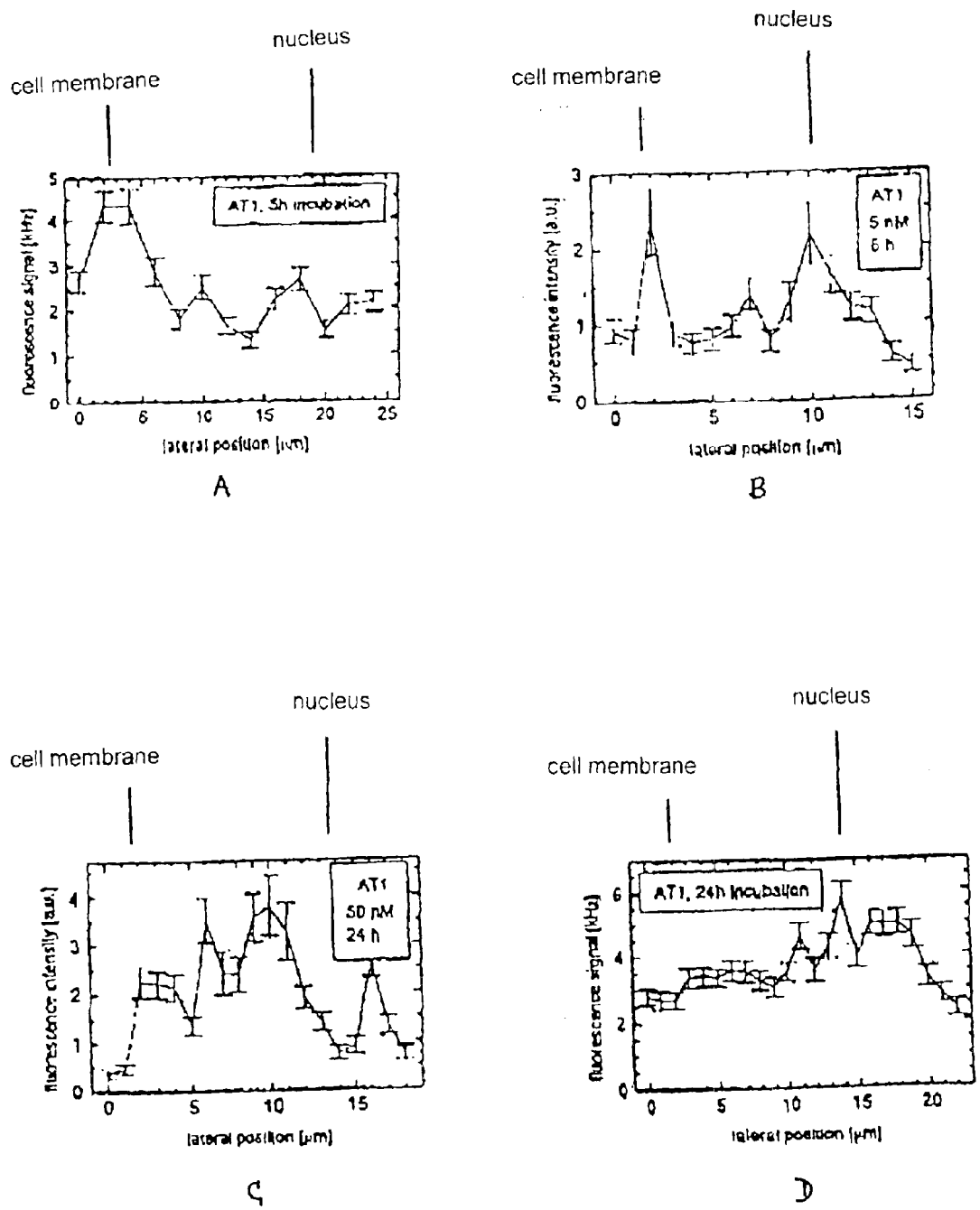
FIG. 3 shows the results of the fluorescence correlation spectroscopy measurement using AT1 cells A) conjugate concentration: 50 nM incubation period: 5 hours B) conjugate concentration: 5 nM incubation period: 5 hours C) conjugate concentration: 50 nM incubation period: 24 hours D) conjugate concentration: 5 nM incubation period: 24 hours.

The conjugate is pursued on its way into the nucleus. For this, a cell is selected and focused under the light microscope. Having focused and set the laser, 100-µm steps are used for passing through the cells, and fluorescence is measured in the form of flashes by photomultipliers. Here, large molecules and small molecules migrate at differing speeds. The number of molecules diffusing in an area of 100 μm each is detected. In this way, the size of the diffused molecules can be determined by means of the duration of the signal. The accompanying diagram is shown in FIG. 3.

In another experiment, the kinetics by which the conjugate reaches the cytoplasm is determined by the same method. The AT-1 cells were again attached for 24 hours. The medium containing the conjugate was used as described above. However, in this case, the fluorescence signal was immediately measured by FCS.

FCS clearly showed a strong accumultation on the cell membrane after an incubation period of 5 hours. Diffusion could not be detected. Only minor amounts of conjugate could be found in the cell menbrame after an incubation period of 24 hours. Attention was then attracted by an accumulation in the nucleus which became even more intense within the observation period of 48 hours.

For the purpose of control conjugates were used in which rhodamine 110 was only bound to either penetratin or NLS. They did not show the above-described effect of nucleus accumulation. If they succeeded at all in penetrating the cell, the conjugates were stopped at the cell membrane of nuclear envelope where they accumulated.

As described analogously above, all of the conjugates produced in Example 1 were studied as regards their time-dependent intracellular transport into the cytoplasm (Z) or the nucleus (N). However, differing from the above-mentioned incubation periods the incubation periods were 1, 3, 6, 10 and 24 hours. The results are shown in Table 1.

EXAMPLE 3

Concentration-Dependent Transport

Figure 4:
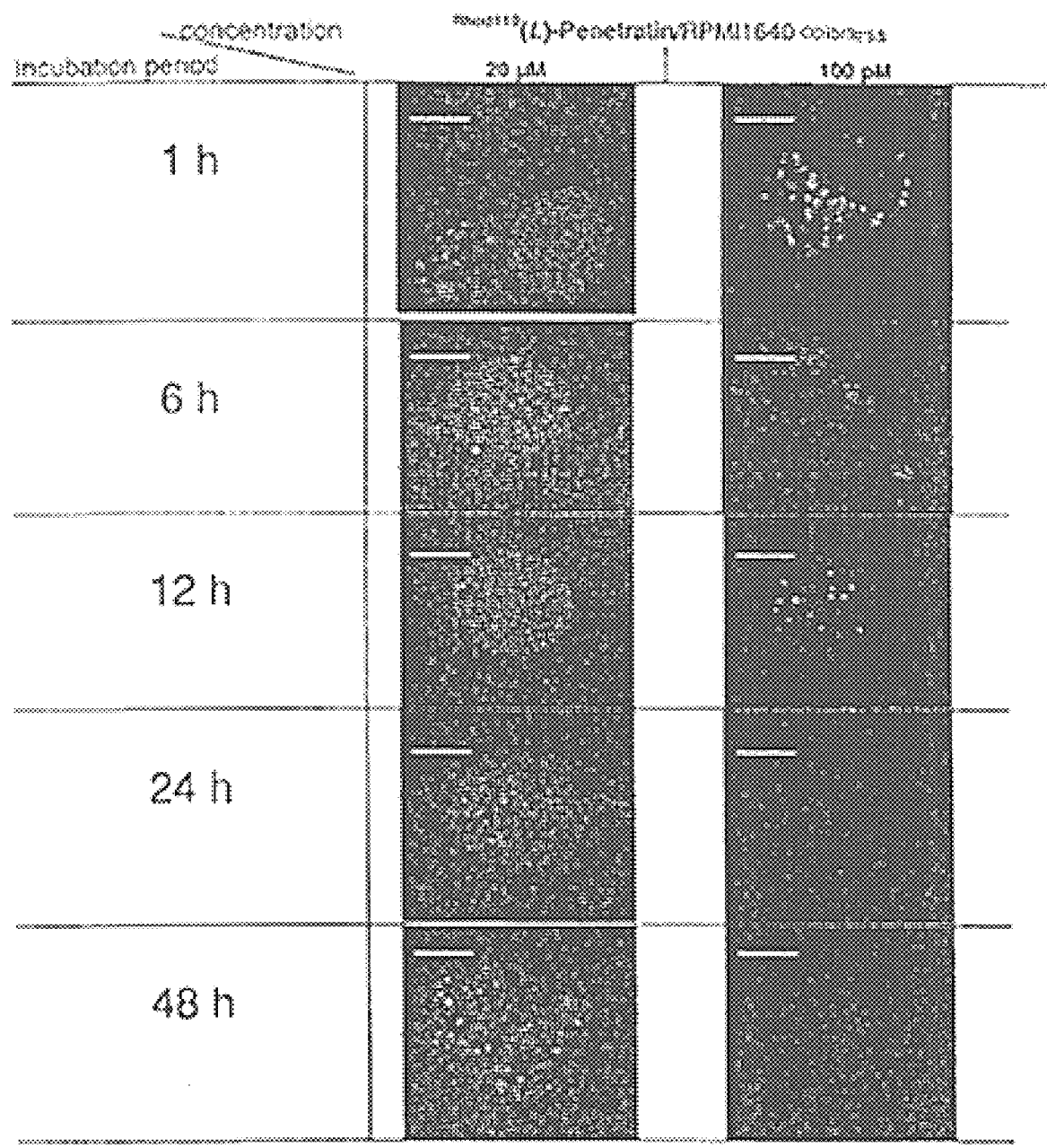
FIG. 4 shows the concentration-dependent and time-dependent transport of $^{rhodamine110}$(L)-penetratin/RPMI medium; DU145 cells: incubation with 20 µM and 100 pM final concentration.
Figure 5:
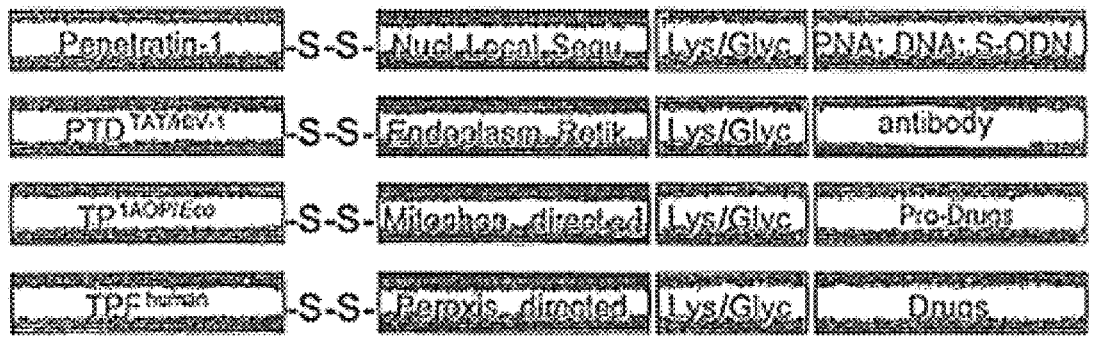
FIG. 5 shows examples of conjugates according to the invention including.

The purpose of the study was to determine to what extent the concentration of the transport peptide $^{rhodamine110}$(L)-penetratin/RPMI medium influences the cellular and nucleus-directed transport in terms of time as well. A comparison was made between the fluorescence of 20 μM and 100 pM final concentration of $^{rhodamine110}$(L)-penetratin/RPMI medium. For this purpose, DU-145 cells were incubated at the indicated concentrations for 1, 6, 12, 24 and 48 hours. Thereafter, washing was carried out three times with RPMI (without penetratin), once with PBS and again with RPMI. Having provided the cells with slide covers, fluorescence was determined directly afterwards by means of CLSM (confocal laser scanning microscopy). The results are shown in FIG. 4. It follows therefrom that at a high concentration of over 20 μM a non-specific transport takes place, which suggests cytotoxicity. However, in a lower concentration there is specific transport into the cytoplasm.

EXAMPLE 4

Inhibition of the Proliferation of AT-1 Cells by Introduction an Anti-Sense Construct Peptide-conjugate constructs according to FIG. 6 were produced using the method described in Example 1 analogously. Here, the active substance was in one case a PNA having the sequence $NH_2$-TAC TGC GAC TCC GG-COOH (anti-sense with respect to rats P2 promoter c-myc=$PNA_{AS}$) (SEQ ID NO: 10)and then a non-sense (random) sequence having the nucleotide sequence $NH_2$-TTA AGG AGG CTC-COOH (=$PNA_{NS}$) (SEQ ID NO: 11).

AT-1 cells were cultured in RPMI 1640, supplemented using 10% FCS, 2 mM glutamine, 100 U/min. penicillin, 100 μg/ml streptomycin.

AT-1 cells are grown on slides for 24 hours. Having changed the medium using dyestuff-free RPMI 1640 (without phenol red), the conjugates (100 nM) are placed onto the cells with RPMI each and incubated at 37° C. and with 5% $CO_2$ for 24, 48, 72 or 96 hours. Thereafter, the conjugate-containing medium is removed and washed twice with 200 μl dyestuff-free RPMI. The cell number of AT-1 cells is determined by means of the Coulter counting method.

Untreated AT-1 cells were used as a control. Unligated $PNA_{AS}$ represents another control. As described analougously above, these controls were incubated with the AT-1 cells.

The result of this experiment is shown in FIG. 7. The proliferation of AT-1 was only inhibited after the administration of the anti-sense construct, i.e. this shows clearly that penetration of the nucleus where the anti-sense sequence can display the desired effect takes only place by means of the construct according to the invention. Unligated anti-sense sequence is as ineffective as the control or a construct which cannot hybridize with one of the AT-1 sequences.

---

What is claimed is:

1. A conjugate for mediating a cell-specific, compartment-specific or membrane-specific transport, wherein the conjugate comprises the following components:
   a transport mediator for passing through the cell membrane,
   a cell-specific, compartment-specific or membrane-specific address protein/peptide; and
   an active substance to be transported, wherein the active substance is covalently linked to the address protein/peptide, and wherein a redox cleavage site is present between the transport mediator and the address protein/peptide.

2. The conjugate according to claim 1, wherein the transport mediator can pass through a plasma membrane.

3. The conjugate according to claim 1, wherein the transport mediator is a member selected from the group consisting of: a penetratin, transportan or parts thereof, bacterial transport protein and viral transport protein.

4. The conjugate according to claim 3, wherein the penetratin has the following sequence:
   $NH_2$-RQIKIWFQNRRMKWKK-(SEQ ID NO: 1).

5. The conjugate according to claim 1, wherein the cell-specific, compartment-specific or membrane-specific address protein or peptide is for import into the nucleus
   $H_3N^+$-Pro-Lys-Lys-Lys-Arg Lys-Val-(=nuclear localization sequence from SV40-T antigen); (SEQ ID NO 6).

6. The conjugate according to claim 1, wherein the active substance is selected from the group consisting of nucleic acids, proteins/peptides and chemical substances.

7. The conjugate according to claim 1, wherein the conjugate has the following structure:
   transport mediator—address protein—active substance.

8. The conjugate according to claim 1, further comprising a spacer.

9. The conjugate according to claim 8, wherein the spacer is located between the address protein and the active substance.

10. The conjugate according to claim 8, wherein the spacer is a member selected from the group consisting of: polylysine, polyethylene glycol and polyvinyl pyrrolidone.

11. A method of preparing a conjugate comprising a transport mediator for passing through the cell membrane, a cell-specific, compartment-specific or membrane-specific address protein/peptide; and an active substance to be transported, the method of preparing, comprising the steps of
   1) synthesizing separate peptides of the transport mediator and address protein/peptide;
   2) forming a covalent bond between the address protein/peptide and the active substance, and
   3) redox coupling of the product from step 2) with the transport mediator by means of redox coupling.

12. The method according to claim 11, wherein the peptide synthesis is carried out according to the Merrifield method.

13. The method according to claim 11, wherein the redox coupling is carried out in an aqueous DMSO solution.

14. The method according to claim 13, wherein a further purification step follows.

15. The method according to claim 14, wherein purification takes place by means of HPLC.

16. A method of transporting a desired active substance into a cell, a cell compartment or through a membrane of the cell, the method comprising:
   contacting a conjugate according to claim 1 with a cell; and
   culturing the cell for a sufficient time for transport of the conjugate into the cell, a compartment of the cell or through a membrane of the cell for transport of the desired active substance therein.

17. A method of delivering a therapeutic agent to a cell in need of such therapeutic agent, the method comprising:
   contacting a conjugate according to claim 3 with the cell; and culturing the cell for a sufficient time for transport of the conjugate and the therapeutic agent into the cell, a compartment of the cell or through a membrane of the cell.

18. The method according to claim 11, further comprising:
   synthesizing a spacer to be covalently bonded between the address protein/peptide and the active substance.

19. The conjugate according to claim 1, wherein the cell-specific, compartment-specific address protein is a nuclear localization sequence from SV40-T antigen.

20. A conjugate for mediating a cell-specific, compartment-specific or membrane-specific transport, wherein the conjugate comprises the following components:
   a transport mediator for passing through a cell membrane or plasma membrane, wherein the transport mediator is a member selected from the group consisting of: a penetratin, transportan or parts thereof, bacterial transport protein and viral transport protein;
   a cell-specific, compartment-specific or membrane-specific address protein/peptide; and
   an active substance to be transported, wherein the active substance is covalently linked to the address protein/peptide, and wherein a redox cleavage site is present between the transport mediator and the address protein/peptide.

* * * * *

UNITED STATES PATENT AND TRADEMARK OFFICE
CERTIFICATE OF CORRECTION

PATENT NO. : 6,821,948 B1
DATED : November 23, 2004
INVENTOR(S) : Klaus Braun et al.

It is certified that error appears in the above-identified patent and that said Letters Patent is hereby corrected as shown below:

Column 2,
Line 61, "CQOH" should be -- "COOH" --

Column 3,
Lines 46 and 51, "N+" should be -- "$N^+$" --
Line 47, "5V40" should be -- "SV40" --

Column 5,
Line 2, "RQIKIWFONRRMKWKK" should be -- "RQIKIWFQNRRMKWKK" --

Column 6,
Line 39, "$^{(IAOP/ECO)}$" should be -- "$^{(IAOP/ECo)}$" --

Column 8,
Line 12, "Introduction" should be -- "Introducing" --

Signed and Sealed this

Seventeenth Day of May, 2005

JON W. DUDAS
*Director of the United States Patent and Trademark Office*

SEQUENCE LISTING

<160> NUMBER OF SEQ ID NOS: 13

<210> SEQ ID NO 1
<211> LENGTH: 16
<212> TYPE: PRT
<213> ORGANISM: Artificial Sequence
<220> FEATURE:
<223> OTHER INFORMATION: Description of the artificial sequence:
      Transport Mediator

<400> SEQUENCE: 1

Arg Gln Ile Lys Ile Trp Phe Gln Asn Arg Arg Met Lys Trp Lys Lys
1               5                   10                  15

```
<210> SEQ ID NO 2
<211> LENGTH: 29
<212> TYPE: PRT
<213> ORGANISM: Artificial Sequence
<220> FEATURE:
<223> OTHER INFORMATION: Description of the artificial sequence: Address
      Peptide

<400> SEQUENCE: 2

Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25

<210> SEQ ID NO 3
<211> LENGTH: 4
<212> TYPE: PRT
<213> ORGANISM: Artificial Sequence
<220> FEATURE:
<223> OTHER INFORMATION: Description of the artificial sequence: Address
      Peptide

<400> SEQUENCE: 3

Lys Asp Glu Leu
1

<210> SEQ ID NO 4
<211> LENGTH: 25
<212> TYPE: PRT
<213> ORGANISM: Artificial Sequence
<220> FEATURE:
<223> OTHER INFORMATION: Description of the artificial sequence: Address
      Peptide

<400> SEQUENCE: 4

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 5
<211> LENGTH: 8
<212> TYPE: PRT
<213> ORGANISM: Artificial Sequence
<220> FEATURE:
<223> OTHER INFORMATION: Description of the artificial sequence: Address
      Peptide

<400> SEQUENCE: 5

Pro Pro Lys Lys Lys Arg Lys Val
1               5

<210> SEQ ID NO 6
<211> LENGTH: 7
<212> TYPE: PRT
<213> ORGANISM: Artificial Sequence
<220> FEATURE:
<223> OTHER INFORMATION: Description of the artificial sequence: Address
      Peptide

<400> SEQUENCE: 6

Pro Lys Lys Lys Arg Lys Val
1               5

<210> SEQ ID NO 7
<211> LENGTH: 3
<212> TYPE: PRT
```

```
<213> ORGANISM: Artificial Sequence
<220> FEATURE:
<223> OTHER INFORMATION: Description of the artificial sequence: Address
      Peptide

<400> SEQUENCE: 7

Ser Lys Leu
1

<210> SEQ ID NO 8
<211> LENGTH: 8
<212> TYPE: PRT
<213> ORGANISM: Artificial Sequence
<220> FEATURE:
<223> OTHER INFORMATION: Description of the artificial sequence: Address
      Peptide

<400> SEQUENCE: 8

Gly Ser Ser Lys Ser Lys Pro Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Description of the artificial sequence: Address
      Peptide

<400> SEQUENCE: 9

Lys Lys Lys Lys Arg Lys Arg Glu Lys
1               5

<210> SEQ ID NO 10
<211> LENGTH: 14
<212> TYPE: DNA
<213> ORGANISM: Artificial Sequence
<220> FEATURE:
<223> OTHER INFORMATION: Description of the artificial sequence: part of
      a PNA

<400> SEQUENCE: 10
tactgcgact ccgg                                                      14

<210> SEQ ID NO 11
<211> LENGTH: 12
<212> TYPE: DNA
<213> ORGANISM: Artificial Sequence
<220> FEATURE:
<223> OTHER INFORMATION: Description of the artificial sequence: part
      of a PNA

<400> SEQUENCE: 11
ttaaggaggc tc                                                        12

<210> SEQ ID NO 12
<211> LENGTH: 11
<212> TYPE: PRT
<213> ORGANISM: Artificial Sequence
<220> FEATURE:
<223> OTHER INFORMATION: Description of the artificial sequence:
      Transport Mediator

<400> SEQUENCE: 12

Tyr Gly Arg Lys Lys Arg Arg Gln Arg Arg
1               5                   10
```

-continued

```
<210> SEQ ID NO 13
<211> LENGTH: 12
<212> TYPE: PRT
<213> ORGANISM: Artificial Sequence
<220> FEATURE:
<223> OTHER INFORMATION: Description of the artificial sequence:
      Transport Mediator

<400> SEQUENCE: 13

Met Thr Arg Gln Thr Phe Trp His Arg Ile Lys His
1               5                   10
```